US011219218B2

(12) United States Patent
Thomas et al.

(10) Patent No.: US 11,219,218 B2
(45) Date of Patent: Jan. 11, 2022

(54) METHODS OF ENHANCING ALGAE PRODUCTION

(71) Applicant: Boise State University, Boise, ID (US)

(72) Inventors: Patrick Thomas, Boise, ID (US); Kevin Feris, Boise, ID (US); Maxine Passero, Boise, ID (US); Gary Dunn, Boise, ID (US)

(73) Assignee: Boise State University, Boise, ID (US)

( * ) Notice: Subject to any disclaimer, the term of this patent is extended or adjusted under 35 U.S.C. 154(b) by 0 days.

(21) Appl. No.: 16/404,150

(22) Filed: May 6, 2019

(65) Prior Publication Data

US 2019/0335755 A1 Nov. 7, 2019

Related U.S. Application Data

(60) Provisional application No. 62/667,917, filed on May 7, 2018.

(51) Int. Cl.
 *C12N 1/12* (2006.01)
 *A01N 59/00* (2006.01)
 *A01G 33/00* (2006.01)

(52) U.S. Cl.
 CPC ............. *A01N 59/00* (2013.01); *A01G 33/00* (2013.01); *C12N 1/12* (2013.01)

(58) Field of Classification Search
 CPC . C02F 3/32; C02F 3/322; A01N 59/00; C12N 1/12; A01H 13/00; A01G 33/00
 See application file for complete search history.

(56) References Cited

U.S. PATENT DOCUMENTS

| 5,176,100 A | 1/1993 | Fujino |
| 6,423,216 B1 | 7/2002 | Turn et al. |
| 8,097,168 B2 | 1/2012 | Theodore et al. |
| 8,101,070 B2 | 1/2012 | Theodore et al. |
| 8,510,985 B2 | 8/2013 | Halachmi Katchanov |
| 2015/0275166 A1 | 10/2015 | Feris et al. |
| 2016/0122705 A1* | 5/2016 | Lancaster ............... C02F 3/325 |
| | | 435/29 |

FOREIGN PATENT DOCUMENTS

JP 2016195586 A * 11/2016

OTHER PUBLICATIONS

Park et al., Bioresource Technology, 2011, 102:35-42 (Year: 2011).*
Zimmo et al., Water Research, 2003, 37:4587-4594 (Year: 2003).*
Factsheet, 2013, downloaded on Apr. 24, 2020 from the website: https://thefishsite.com/articles/managing-ammonia-in-fish-ponds (Year: 013).*

(Continued)

*Primary Examiner* — Allison M Fox
*Assistant Examiner* — Qing Xu
(74) *Attorney, Agent, or Firm* — McKee, Voorhees & Sease, PLC (57) ABSTRACT

Method of inhibiting live grazing organisms in an algae composition are disclosed, which do not inhibit the algae. In certain embodiments the concentration of algae increases. In other embodiments the mortality of live grazing organisms is complete. The method contacts an algae composition with wastewater comprising free ammonia and maintaining pH of at least 8 for more than two hours.

8 Claims, 5 Drawing Sheets

(56) References Cited

OTHER PUBLICATIONS

Printout of conversion table of un-ionized ammonia by pH and temperature, downloaded on Nov. 25, 2019 from the website: https://support.hach.com/app/answers/answer_view/a_id/1011356/~/ammo. (Year: 2019).*

Abeliovich et al., "Toxicity of Ammonia to Algae in Sewage Oxidation Ponds", Applied and Environmental Microbiology, vol. 31, No. 6, pp. 801-806, Jun. 1976.

Arthur et al., "Seasonal Toxicity of Ammonia to Five Fish and Nine Invertebrate Species", Bull. Envion. Contam. Toxicol., vol. 38, pp. 324-331, 1987.

Bartley et al., "pH effects on growth and lipid accumulation of the biofuel microalgae Nannochloropsis salina and invading organisms", J. Appl. Phycol., vol. 26, pp. 1431-1437, 2014.

Carney et al., "Parasites in algae mass culture", Frontiers in Microbiology, vol. 5, Article 278, 8 pages, Jun. 2014.

De Araujo et al., "Effect of unionized ammonia, viscosity and protozoan contamination on the enzyme activity of the rotifer Brachionus plicatilis", Aquaculture Research, vol. 31, pp. 359-365, 2000.

Gersich et al., "Site-Specific Acute and Chronic Toxicity of Ammonia to Daphnia Magna Straus", Environmental Toxicology and Chemistry, vol. 5, pp. 443-447, 1986.

Gutierrez et al., "Ammonia inhibition in oleaginous microalgae". Algal research, vol. 19, pp. 123-127, Jul. 26, 2016.

Lincoln et al., "Zooplankton Control in Mass Algal Cultures", Aquacultures, vol. 32, pp. 331-337, 1983.

Schlüter et al., "The Inhibition by Ammonia of Population Growth of the Rotifer, Brachionus Rubens, in Continuous Culture", Aquaculture, vol. 46, pp. 215-220, 1985.

Tan et al., "Outdoor cultures of Chlorella pyrenoidosa in the effluent of anaerobically digested activated sludge: The effects of pH and free ammonia", Bioresource Technology, vol. 200, pp. 606-615, 2016.

Thomas et al., "Free ammonia offers algal crop protection from predators in dairy wastewater and ammonium-rich media", Biosource Technology, vol. 243, pp. 724-730, Jul. 3, 2017.

Thomas, Patrick, "Effects of Algal Diversity on Productivity and Grazing Resistance in Dairy Wastewater", http://scholarworks.boisestate.edu/cgi/viewcontent.cgi?article=2175&ano&context=td, 105 pages, 2016.

Van Ginkel et al., "Taking advantage of rotifer sensitivity to rotenone to prevent pond crashes for algal-biofuel production", Algal Research, vol. 10, pp. 100-103, Mar. 22, 2015.

Wang et al., "Anaerobic digested dairy manure as a nutrient supplement for cultivation of oil-rich green microalgae *Chlorella* sp.", Bioresource Technology, vol. 101, pp. 2623-2628, 2010.

Xu et al., "The Use of the Schizonticidal Agent Quinine Sulfate to Prevent Pond Crashes for Algal-Biofuel Production", Int. J. Mol. Sci, vol. 16, pp. 27450-27456, Nov. 17, 2015.

\* cited by examiner

METHODS OF ENHANCING ALGAE PRODUCTION

REFERENCE TO RELATED APPLICATION

This application claims priority to previously filed and provisional application U.S. Ser. No. 62/667,917, filed May 7, 2018, the contents of which are incorporated herein by reference in its entirety.

STATEMENT REGARDING FEDERALLY SPONSORED RESEARCH OR DEVELOPMENT

This invention was made with Government support under contract USDA-NIFA-#2012-68002-19952 awarded by the United State Department of Agriculture. The Government has certain rights in the invention.

BACKGROUND

In order to meet ambitious targets for quickly reducing greenhouse gas emissions, a diverse portfolio of low-carbon energy sources will be needed. Advanced biofuels and bio-products from microalgae have considerable potential to help meet these goals. Algae are much more productive than terrestrial biofuel crops, leading to greater yields of biofuel per unit area (Chisti, 2008, 2007; Jones and Mayfield, 2012). Moreover, algae can be grown on marginal land using brackish water or wastewater, which reduces the food vs. fuel issues associated with first generation biofuel crops (Chisti, 2008, 2007; Jones and Mayfield, 2012). Mass algal cultivation could even promote reforestation and carbon capture by displacing conventional animal feed crops (Walsh et al., 2015).

Despite the many benefits of harnessing algae biomass for a variety of bio-products, there are still barriers that must be overcome to enhance the viability of such systems. Competition with inexpensive petroleum fuels makes algal biofuel less viable and incentivizes industry to pursue higher-value but lower-volume products like nutraceuticals. Therefore, mass commercialization of algae will require minimization of production costs. Additionally, there are many grazing pests (e.g. rotifers, ciliates and cladocerans) and pathogens (e.g. bacteria, viruses, and fungi) that can cause mass algal cultures to crash, reducing annual productivity (Day, 2013; Shurin et al., 2013). For example, grazers like rotifers exert particularly strong top-down pressure on algae; *Brachionus plicatilis* can consume up to 3000 cells per hour (Montagnes et al., 2001) which causes cultures to crash if left untreated (Van Ginkel et al., 2015). Development of cost-effective methods for protecting algal crops against pests and pathogens is therefore vital for the successful scale up of the algae biomass industry.

SUMMARY

Methods of inhibiting live grazing organisms in an algae composition are disclosed, which methods do not inhibit algae. In certain embodiments the mortality of live grazing organisms is complete. Other embodiments provide for an increase in algae concentration. Still further embodiments provide the; live grazing organisms are rotifers. The method contacts the algae composition with wastewater comprising free ammonia and maintaining pH of at least 8 for more than two hours. Further embodiments maintain the pH at 8 to 9. Embodiments provide the concentration of free ammonia is at least 17 mg $L^{-1}$. Additional embodiments provide the composition is contacted with the wastewater for at least six hours. Compositions comprising the same are also disclosed.

BRIEF DESCRIPTION OF THE DRAWINGS

FIGS. 5A and B show a graph A) of algae densities and a bar chart (B) of effect of free ammonia exposure on algae. A) Densities of *N. oculata* over time when cultured with *B. plicatilis* in ADE medium, and subjected to different elevated free ammonia exposure times. C: rotifer-free control. Points and bars represent mean±SEM and symbols represent different exposure times in hours. B) Effect of free ammonia exposure time on AFDW of *N. oculata* (mean±SEM) when cultured with *B. plicatilis* in ADE medium ($F_{5,5.27}$=27.7, p=0.0009). C: rotifer-free control.

DESCRIPTION

Cost-effective methods for protecting crops from grazing organisms like rotifers are needed to reduce the risk of pond crashes in mass algal cultures. We present a novel strategy to optimize the exposure time to free ammonia, via control of media pH, in both defined media and wastewater such as dairy anaerobic digester effluent to suppress pests such as rotifers and maintain algal productivity.

In order to meet ambitious targets for quickly reducing greenhouse gas emissions, a diverse portfolio of low-carbon energy sources will be needed. Advanced biofuels and bio-products from microalgae have considerable potential to help meet these goals. Algae are much more productive than terrestrial biofuel crops, leading to greater yields of biofuel per unit area (Chisti, 2008, 2007; Jones and Mayfield, 2012). Moreover, algae can be grown on marginal land using brackish water or wastewater, which reduces the food vs. fuel issues associated with first generation biofuel crops (Chisti, 2008, 2007; Jones and Mayfield, 2012). Mass algal cultivation could even promote reforestation and carbon capture by displacing conventional animal feed crops (Walsh et al., 2015).

Despite the many benefits of harnessing algae biomass for a variety of bio-products, there are still barriers that must be overcome to enhance the viability of such systems. Competition with inexpensive petroleum fuels makes algal biofuel less viable and incentivizes industry to pursue higher-value but lower-volume products like nutraceuticals. Therefore, mass commercialization of algae will require minimization of production costs. Additionally, there are many grazing pests (e.g. rotifers, ciliates and cladocerans) and pathogens (e.g. bacteria, viruses, and fungi) that can cause mass algal cultures to crash, reducing annual productivity (Day, 2013; Shurin et al., 2013). For example, grazers like rotifers exert particularly strong top-down pressure on algae; *Brachionus plicatilis* can consume up to 3000 cells per hour (Montagnes et al., 2001) which causes cultures to crash if left untreated (Van Ginkel et al., 2015). Development of cost-effective methods for protecting algal crops against pests and pathogens is therefore vital for the successful scale up of the algae biomass industry.

One prevalent strategy for eliminating pests from algal cultures is to use chemical controls that selectively eliminate the pest while minimizing harm to the algae. This approach has been effective for inhibiting rotifer growth using free ammonia, copper, rotenone, hypochlorite and quinine (Lincoln et al., 1983; Pradeep et al., 2015; Schlüter and Groeneweg, 1985; Van Ginkel et al., 2015; Xu et al., 2015) and also for inhibiting chytrid fungi using hydrogen peroxide (Carney and Lane, 2014). All of these inputs are effective at inhibiting pests without severely affecting algae. Ammonia, however, could be particularly efficient as addition of ammonium could play a double role as fertilizer for algae and as a broad-spectrum inhibitory agent for grazing pests like rotifers and cladocerans (Arthur et al., 1987; Gersich and Hopkins, 1986; Lincoln et al., 1983; Schlüter and Groeneweg, 1985). Specifically, free ammonia ($NH_3$) reduces *Brachionus* rotifer reproduction at concentrations as low as 2.4 mg/L (de Araujo et al., 2000) and causes complete mortality at concentrations over 5 mg/L free $NH_3$—N (Schlüter and Groeneweg, 1985). Algae are generally much less sensitive to free ammonia, although this varies by strain. *Scenedesmus obliquus* can tolerate up to 28 mg/L free $NH_3$—N(Abeliovich and Azov, 1976) and *Chlorella pyrenoidosa* can tolerate up to 20 mg/L free $NH_3$—N(Tan et al., 2015) without inhibition of photosynthesis or growth rate. Similarly, *Nannochloropsis oculata* and *Chlorella sorokiniana* were not inhibited by the highest level tested (16 mg free $NH_3$—N), although other species were inhibited (Gutierrez et al., 2016). Importantly, the lipid content of *N. oculata* was not significantly altered with exposure to high free ammonia levels, indicating that ammonia will not affect the species' biomass composition relevant to biofuels production (Gutierrez et al., 2016).

Additionally, ammonium concentrations are often very high in wastewaters, so a simple manipulation of pH when ammonium levels are high could be used as an integrated pest management strategy. Dairy anaerobic digester effluent (ADE), for example can have over 2000 mg/L total $NH_3$—N(Wang et al., 2010). By allowing pH to rise via photosynthesis, to levels that increase the free ammonia fraction, a pond operator could selectively inhibit rotifers at very low or no overall cost, as no additional chemical inputs are needed, and without reduction of algal productivity. Minimizing not only direct costs, but also indirect costs associated with crop protection strategies is vital to sustainable production; environmental and societal costs of agricultural pesticide use have been estimated at $10 billion yr$^{-1}$ (Pimentel, 2005), which the nascent algae biomass industry would be wise to avoid. In contrast to other recent breakthroughs in algal crop protection (Carney and Lane, 2014; Pradeep et al., 2015; Van Ginkel et al., 2015; Xu et al., 2015), using ammonia already inherent to the wastewater requires neither input costs nor application of exogenous chemical compounds.

Despite the potential for free ammonia dosing to minimize rotifer invasions without harming algal growth, there has been very little research into specific methods for taking advantage of this promising strategy. Tan et al. (2015) suggest that strategic control of free ammonia levels in wastewater could be used simultaneously to inhibit pests while minimizing effects on algal biomass. To our knowledge, however, no study has investigated the effects of exposure time of elevated free ammonia levels on rotifers or algae. We therefore sought to provide novel insights into the optimization of this strategy by experimentally manipulating free ammonia exposure time, with the goal of identifying levels with both maximum algal productivity and maximum grazer control. To accomplish this, we employed a model saltwater algal species, *Nannochloropsis oculata*, as a representative strain commonly used for large-scale outdoor cultivation of biofuels and bioproducts, as well as the saltwater rotifer *Brachionus plicatilis*, as a representative model grazer capable of rapidly depleting algal cultures. We first subjected each species to a gradient of free ammonia concentrations to verify toxicity levels, and subsequently exposed both species in co-culture to different free ammonia times. Specifically, the objectives of this research were to 1) identify effects of free ammonia concentration on the rotifer *Brachionus plicatilis* in both defined media and dairy wastewater after a 24 hour exposure time, 2) identify effects of free ammonia concentration on the saltwater algae species *Nannochloropsis oculata* in both defined media and dairy wastewater after a 24 hour exposure time, and 3) identify effects of free ammonia exposure time on longer-term algal productivity in both defined media and dairy wastewater in the presence of *B. plicatilis* rotifers. We hypothesized that increasing free ammonia exposure time would decrease rotifer survival, and that when co-cultured with rotifers, algal production would be highest at an optimum point where rotifers are inhibited but algae are not.

The present process and composition are to methods of protecting algae from grazing organisms. When referring to grazing, organisms is meant to describe zooplankton that feed on algae. Examples include rotifers, that is the multicellular aquatic animal of the phylum Rotifera; ciliates, single celled protozoan animals of the phylum Ciliphora; and cladocerans, branchiopod crustaceans of the order Cladocera. Examples of rotifers, without intending to be limiting, are *Bracius* sp. and *Phiodina* sp. In the process the algae is contacted with a media composition that contains ammonia.

The inventors here have shown that free ammonia in wastewater provides a source of ammonia that reduces grazing organisms on algae without inhibition of algae. Inhibition of rotifers occurs when reproduction rate is lowered and/or the rotifer dies. This can be measured by any convenient mechanism, and one means is to determine the concentration of rotifer population in a known volume to determine if the population increases, stays the same, or decreases. The rotifer is inhibited when the population does not increase, and preferably, decreases. In an embodiment the rotifer population mortality is complete. This occurs without inhibition of algae by reducing growth rates and/or causing death of the algae. Concentration of the population of algae stays the same or increases.

Further, adjustment of pH impacts algae growth, allowing increase of growth of algae at preferred pH levels. An embodiment provides the pH is at least 8, and a preferred embodiment provides the pH is 8 to 9. Still a further embodiment provides the pH is 9.

Embodiments provide the contact of the free ammonia at the described pH is maintained for more than two hours. Certain embodiments provide for exposure to free ammonia and maintaining the pH for at least 24 hours. Still further embodiments provide for free ammonia exposure and maintaining the pH for at least six hours, and in a preferred embodiment for six to 12 hours. The result is a decrease in density of living grazing organisms which not inhibiting algae, and increasing algae concentrations. A preferred embodiment provides that the composition comprising ammonia is wastewater, thereby reducing cost of the process. No additional chemical compositions need to be added to obtain reduction in numbers or density of live grazing organisms.

Still further embodiments provide the concentration of free ammonia is at least 7.0 mg $L^{-1}$, 8.0 mg $L^{-1}$, 8.5 mg $L^{-1}$, 9.0 mg $L^{-1}$, 9.5 mg $L^{-1}$, 10.0 mg $L^{-1}$, 10.5 mg $L^{-1}$, 11.0 mg $L^{-1}$, 11.5 mg $L^{-1}$, 12.0 mg $L^{-1}$, 12.5 mg $L^{-1}$, 13.0 mg $L^{-1}$, 13.5 mg $L^{-1}$, 14.0 mg $L^{-1}$, 14.5 mg $L^{-1}$, 15.0 mg $L^{-1}$, 15.5 mg $L^{-1}$, 16.0 mg $L^{-1}$, 16.5 mg $L^{-1}$, 17.0 mg $L^{-1}$, 17.5 mg $L^{-1}$, 18.0 mg $L^{-1}$, 18.5 mg $L^{-1}$, 19.0 mg $L^{-1}$, 19.5 mg $L^{-1}$, 20.0 mg $L^{-1}$, 20.5 mg $L^{-1}$, 21.0 mg $L^{-1}$, 21.5 mg $L^{-1}$, or more or amounts in-between.

In an embodiment the process provides for complete mortality of the grazing organism. The number of live organisms may be decreased to zero. Measurement of live grazing organisms may be made by any convenient method, and for example, without limitation, by measuring density of dry weight or ash free dry weight (AFDW) of the composition.

Further, it has been found that the growth of algae is increased with the process compared to a process not exposing the algae to the ammonia-containing composition at the above pH for the described exposure time. Such growth may be measured by any available method, such as cell density growth rate or growth stage or any other useful method.

Also provided are wastewater compositions having increased algae biomass production and reduced live grazing organism numbers/density as a result of combining the algae with a wastewater composition comprising ammonia at the pH and exposure times described above. The composition may in one embodiment comprise a cultivation pond.

Algae are a diverse group of eukaryotic organisms that contain chlorophyll and carry out photosynthesis but lack true roots, stems and leaves, and can be found in fresh or salt water or moist soil. Algae occur in a wide range of forms from microscopic to macroscopic e.g. seaweeds, some of which are up to 30 meters long. Microscopic algae exist as, for example, single cells e.g. diatoms, in colonies e.g. Volvox or in filaments e.g. Spirogyra, and the like.

Wastewaters may be used as a source of ammonia in one embodiment. A further embodiment preferably provides agricultural wastewaters resulting from animal production or contained animal feeding operation (CAFO) sites, although the process can include the use of industrial, municipal, and other wastewater sources containing ammonia. In other embodiments, wastewater can come from agricultural production such as dairy farms. Examples of dairy wastewater include dairy manure wastewaters, anaerobic digester effluent (ADE) and polyhydroxyalkanoate reactor effluent (PHAE). Full-strength agricultural wastewater or a lower concentration diluted with water to achieve an acceptable light absorbance (generally 5%) can be used as a "growth medium" for sustaining rapid growth of algae strains. A discussion of wastewater and its use in algal production is found at US Patent Application No. 20150275166. This reference and references cited herein are incorporated herein by reference in their entirety.

The pH of the composition can be controlled through the use of a buffer, carbon dioxide, or by addition of an acid or base at the beginning or during the course of the growth cycle. In some cases, both an acid and a base can be used in different zones of the culture or raceway or in the same zone at the same or different times in order to achieve a desirable degree of control over the pH. Non-limiting examples of buffer systems include, for example, carbon dioxide, phosphate, TRIS, TAPS, bicine, tricine, HEPES, TES, MOPS, PIPES, cacodylate, MES, acetate, and the like. Non-limiting examples of acids include, for example, sulfuric acid, hydrochloric acid, lactic acid, acetic acid, and the like. Non-limiting examples of bases include, for example, potassium hydroxide, sodium hydroxide, ammonium hydroxide, ammonia, sodium bicarbonate, calcium hydroxide, sodium carbonate, and the like. Some of these acids and bases, in addition to modifying the pH, can also serve as nutrients for the cells, while carbon dioxide can serve as the carbon source for photosynthesis and carbon storage.

The pH in an embodiment of process may be controlled by allowing pH to rise via photosynthesis. The shifts in pH due to photosynthesis will be dependent on algal cell densities, incubation temperature and light intensity. The process is dependent on $CO_2$ assimilation by photosynthesis to increase the solution pH. By way of example without limitation, pH shift may be quite rapid, and may be within one to three hours from the start of photosynthesis. The pH of the culture can be controlled to approximate a constant value throughout the entire course of the growth cycle, or it can be changed during the growth cycle. Such changes can be used, for example, to initiate or terminate different metabolic pathways, to force production of one particular product, to force accumulation of a product such as fats, dyes, or bioactive compounds, to suppress growth of other microorganisms, to suppress or encourage foam production, to force the cells into dormancy, to revive them from dormancy, or the like.

Free ammonia offers algal crop protection from predators in wastewater and ammonium-rich media. The following is presented by way of exemplification and not intended to limit the scope of the processes and compositions.

EXAMPLES

In one experiment, we tested five different free ammonia exposure times (0, 1, 2, 6, and 12 hours) while controlling for pH effects and found a significant nonlinear effect of ammonia exposure time on rotifer survival (p<0.0001), but no effect of pH on rotifer survival (p>0.9). In both media types, 6-12 hours of elevated free ammonia significantly reduced Brachionus plicatilis rotifer survival with no negative effects on the alga Nannochloropsis oculata. Shorter exposure times were insufficient to inhibit B. plicatilis, leading to severe grazing-induced crashes in N. oculata cultures. These results suggest that algal crops can be protected from rotifers with no productivity loss, and at minimal operational cost, by elevating free ammonia levels for 6 or more hours.

Materials and Methods

Media and Cultures

Instant Ocean® sea salts (33.6 g L$^{-1}$, Spectrum Brands, Blacksburg, Va., USA) was used to create artificial seawater (hereafter referred to as "ASW") for all media used. F/2 media was prepared by enriching ASW with f/2 nutrients according to a UTEX standard recipe. From these base media types, we created a defined medium treatment with added ammonium at approximately the same free $NH_3$—N level as 5% ADE treatment. This solution was composed of f/2 nutrients in ASW and added $NH_4Cl$ (mean 113.9±2.90 mg L$^{-1}$ total $NH_3$—N across trials), which is hereafter referred to as "f/2 medium." We also created a solution containing ASW with 5% ADE (mean 136.8±6.30 mg L$^{-1}$ total $NH_3$—N across trials) to assess effects of ammonia in undefined wastewater-based media; this medium is hereafter referred to as "ADE medium." A 5% concentration of ADE was chosen based on previous research indicating that this dilution maximizes growth rates and nutrient removal (Passero et al., 2015). While there were slight differences in initial $NH_3$—N concentrations between the two media types, they were small when compared to the experimental manipulation of free ammonia, which spanned two orders of magnitude for each treatment. Dairy ADE was collected from Big Sky West Dairy, Gooding, Id., USA, was stored at −20° C., and was centrifuged prior to use in experiments to reduce potential effects of particulate organic matter. ADE was centrifuged at 10,000 rpm for 10 min for well plate experiments and 20 min for the exposure time experiment. Conductivity of the media was measured before use; 5% ADE medium had a conductivity of 0.2 mS/cm, while the ASW medium had a conductivity of 47 mS/cm. This 4% increase in conductivity upon addition of ADE had no noticeable effects on the species studied.

We obtained *B. plicatilis* L-type rotifers from Reed Mariculture, Campbell, Calif., USA. These rotifers were cultured in ASW with *N. oculata* as a food source and received a 50% exchange by volume approximately one week prior to experiments. *N. oculata* (product code FO-PT2-NANN) was obtained from AquaCave, Inc., Gurnee, Ill., USA. *N. oculata* was cultured on f/2 medium and was in stationary phase upon use in all experiments. Stationary phase cells were chosen with the goal of best reflecting the physiological state of mass algal cultures upon a harvesting and re-dilution event.

Manipulation of pH to Assess Ammonia Toxicity to *B. plicatilis* in Artificial Seawater and Dairy ADE Media Three separate 24-well plate experiments were used to assess the effects of both free ammonia and pH on *B. plicatilis* in both defined and undefined media. These consisted of: 1) an experimental plate using ASW medium with added $NH_4Cl$, 2) an experimental plate using ASW with 5% dairy ADE medium, and 3) a control plate (with no $NH_3$—N addition) using ASW. All precursor solutions also received 0.01 M Tris base to buffer pH. These solutions were then separated into each pH treatment and were adjusted to designated pH levels (7, 7.5, 8, 8.5, and 9; measured by Denver Instruments UP-10 meter) using 1 M HCl in 50 mL centrifuge tubes, thereby varying pH for both the control and free ammonia experimental plates, prior to aliquoting to the 24-well plates for the $NH_3$ exposure experiments. At this point, $NH_4Cl$ was added to the pH-adjusted Tris/ASW solutions to yield an estimated 113.9±2.90 mg L$^{-1}$ total $NH_3$—N in the experimental (ASW+$NH_4Cl$) plate. The same procedure was carried out for the ASW+5% ADE plate, but with 5% ADE (134.17±14.1 mg L$^{-1}$ total $NH_3$—N in this experiment) as the ammonium source instead of $NH_4Cl$. The control solutions received the same treatment in terms of pH manipulation and addition of buffer solution, but with no source of added ammonium. Estimated initial free ammonia concentrations for the ASW+$NH_4Cl$ medium were 0.65 mg L$^{-1}$ (at pH 7), 2.04 mg L$^{-1}$ (at pH 7.5), 6.2 mg L$^{-1}$ (at pH 8), 17.54 mg L$^{-1}$ (at pH 8.5), and 41.6 mg L$^{-1}$ (at pH 9) for each treatment, respectively. Estimated initial free ammonia concentrations in ADE medium were 0.77 mg L$^{-1}$ (at pH 7), 2.39 mg L$^{-1}$ (at pH 7.5), 7.29 mg L$^{-1}$ (at pH 8), 20.6 mg L$^{-1}$ (at pH 8.5), and 48.9 mg L$^{-1}$ (at pH 9) for each treatment, respectively. Each pH treatment was carried out in quadruplicate with a final volume of 1.5 mL per well. Using a dissecting scope and a micropipette, 10 live *B. plicatilis* rotifers were added to each well for all three 24-well plates. All plates were incubated under a 12:12 hour light/dark cycle under 25 μE m$^{-2}$ s$^{-1}$ illumination by fluorescent lights at room temperature for 48 hours. Note that photoperiod and light intensity were controlled for within each experiment, but that light levels differed with experimental settings, and that experiments involving *N. oculata* received greater light intensity to allow for maximum algal production (however, light levels are not expected to alter availability of free ammonia). Live rotifers were enumerated at 24 and 48 hours using a dissecting scope at 12-16× total magnification. Moving rotifers were counted as living whereas rotifers displaying no movement for several seconds were not counted as alive.

Manipulation of pH to Assess Ammonia Toxicity to the Model Algae Species *N. oculata* in f/2 and Dairy ADE Media Similar methods to those in Section 2.2 were followed to make the pH-adjusted ASW/Tris base treatment solutions for the 24 well plates containing *N. oculata*. However, the defined medium contained ASW enriched with f/2 nutrients instead of solely ASW. A volume of 100 μL of inoculum of *N. oculata* was added to each well to yield an initial $OD_{680}$ of approximately 0.1. The ADE medium was identical to that in Section 2.1, except for the addition of *N. oculata* instead of *B. plicatilis*. All wells had a final volume of 1.5 mL and all pH treatments were carried out in quadruplicate. All 24-well plates were incubated under 102 μE m$^{-2}$ s$^{-1}$ illumination by fluorescent lights on a 12:12 hour light/dark cycle at room temperature for seven days. Algal growth was monitored by measuring optical density at 680 nm ($OD_{680}$) in situ in the 24 well plates used every 24 hours for 7 days.

Manipulation of Free Ammonia Exposure Time in Mixed Cultures of Algae and Rotifers Five free ammonia exposure times were chosen (0, 1, 2, 6, and 12 hours) with the goal of identifying which times may lead to an optimal reduction of *B. plicatilis* populations without negatively affecting *N. oculata* growth. We also used a rotifer-free control to observe the growth of *N. oculata* with neither rotifers nor elevated free ammonia exposure relative to experimental treatments. We conducted this experiment in both defined media (f/2) and dairy wastewater (ADE) to observe any differences between media types. For the defined medium trial, we created culture mixtures containing f/2 in ASW, 0.01 M Tris base, *N. oculata* at approximately 1×10$^6$ cells mL$^{-1}$ and *B. plicatilis* at approximately 10 rotifers mL$^{-1}$. $NH_4Cl$ was added to this mixture to initiate the period of free ammonia exposure. Similarly, for the dairy wastewater trial, we created culture mixtures containing ASW, 0.01 M Tris base, *N. oculata* at approximately 1×10$^6$ cells mL$^{-1}$, and *B. plicatilis* at approximately 10 rotifers/mL. The initial cell density of *N. oculata* was meant to represent a high-density culture nearing early stationary phase, which also allowed for increases in cell density. The initial rotifer density was chosen to represent initial stages of a contamination event after exposure of the algal culture to colonizing rotifer pests, at which point contamination is detectable yet treatable. ADE was added to this mixture to initiate the period of free ammonia exposure. For both trials, pH was immediately adjusted to 9 for the 1, 2, 6, and 12 hour treatments and held at this pH for the designated exposure time. The 0 hour and control treatments were adjusted to pH 6.3-6.5 via $CO_2$ addition prior to addition of the ammonium source, thereby eliminating any exposure to elevated free ammonia. Once each treatment had reached its designated exposure time, we manually lowered pH via once daily addition of $CO_2$ to the target low point of between 6.3-6.5 (chosen to minimize free ammonia) and maintained this pH range for the remainder of the experiment. Thus, all treatments within an experiment received the same amount of $CO_2$ and the same amount of total $NH_3$—N. Flasks were shaken and stirred once daily on a stir plate while pH was being adjusted to desired level. In this experiment, pH was measured and controlled in each treatment using American Marine Pinpoint pH controllers.

Samples for total $NH_3$—N were collected at the beginning and end of the exposure time for each treatment in order to quantify potential loss of N from the system caused by volatilization of free ammonia. Densities of *N. oculata* and *B. plicatilis* were measured at the initial free ammonia exposure time, and every 24 hours thereafter for eight days. Live *B. plicatilis* were enumerated in triplicate 1 mL counts in a Sedgewick-Rafter counting chamber (Wildco item #EW-05491-64), and growth of *N. oculata* was tracked by both $OD_{680}$ measurement and direct cell counts. Final ash free dry weight (AFDW) was measured on day eight for all replicates.

All treatments were carried out in triplicate in 500 mL Erlenmeyer flasks equipped with stoppers and sampling tubes and had final culture volumes of 250 mL. Flasks were incubated under $130.5 \pm 4.7$ $\mu E$ $m^{-2}$ $s^{-1}$ illumination by fluorescent lights on a 12:12 hour light/dark cycle at room temperature for eight days. After the initial 24-hour ammonia dosing and recovery period, the average daily low and high pH levels were $6.47 \pm 0.02$ and $7.27 \pm 0.04$, respectively, in f/2 medium. Similarly, high and low pH levels were $6.44 \pm 0.01$ and $7.55 \pm 0.02$, respectively, in ADE medium. We chose this range in order to eliminate possible free ammonia inhibition after the designated exposure period while also staying within the pH range for optimal growth of *N. oculata*. For example, even if we assume that total $NH_3$—N was at its high initial level, free ammonia would have ranged from 0.2 mg $L^{-1}$ (at pH 6.44) to 2.9 mg $L^{-1}$ (at pH 7.55), which represent concentrations that do not affect even more sensitive algae species (Gutierrez et al., 2016).

Algal Growth Response Measurements $OD_{680}$ was determined by pipetting a 200 $\mu$L sample onto a 96 well plate and measured using a Biotek Instruments Synergy Mx 96 well plate reader (part no. 7191000). Samples for direct cell counts were preserved in 2% Lugol's iodine upon sampling and refrigerated until enumeration. Direct cell counts were taken using Neubauer hemocytometers; a 10 $\mu$L undiluted sample was inserted and cells were counted at 400× total magnification and converted to cell density in cells/ml.

All measurements for dry weight (DW) and ash-free dry weight (AFDW) were performed according to a modified version of EPA method 340.2. Pre-rinsed and pre-combusted glass fiber filters (Data Support Co., Inc, part no. GEN47MM, 1.5 $\mu$m pore size) were used to filter a 10 mL volume of algae culture. The samples were dried overnight at 105° C., weighed, combusted at 500° C., and re-weighed.

Determination of Free Ammonia Concentration

Samples for total $NH_3$—N analysis were filtered through a 0.45 $\mu$m syringe tip filter, acidified to <pH 2, and stored at −20° C. prior to analysis. A Lachat QuikChem® Series 8500 flow injection analysis system was used to analyze total dissolved $NH_3$—N; total dissolved $NH_3$—N levels were determined using QuikChem® Method 10-107-06-1-F. All samples were diluted sufficiently to be within the required range for this method. With known initial total $NH_3$—N and initial pH levels, we calculated the initial free $NH_3$—N concentration using the Henderson-Hasselbach equation.

Statistical Analysis

All statistical analyses were performed in JMP Pro 12.0.1. Linear regression was used to determine the effect of initial free ammonia level and exposure time on growth of *N. oculata* and *B. plicatilis*. Rotifer survival data was log-transformed to meet the assumption of normal distribution for linear regression for datasets which were not normally distributed. One-way Welch's ANOVAs were used to detect differences in AFDW and final cell density among exposure time levels for the flask experiment. Growth rates were estimated using the Logistic three-parameter growth models in the Fit Curve function in JMP Pro 12 (the three parameters in this model are growth rate, inflection point, and asymptote). All values in the text and figures are reported as mean±standard error of the mean (SEM) unless otherwise stated. Initial free ammonia experiments were conducted in quadruplicate and free ammonia exposure time experiments were conducted in triplicate.

Results and Discussion

Figure 1A:
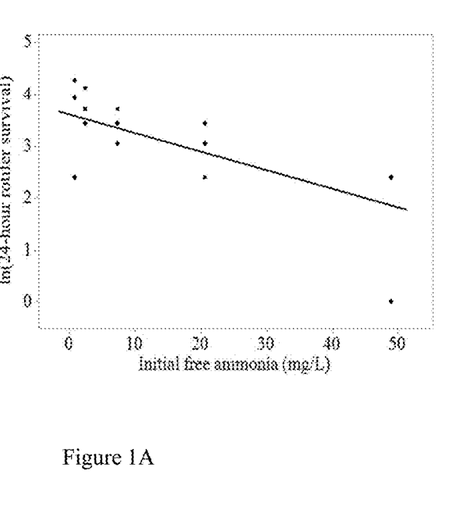
FIGS. 1A and B are two graphs. (A) Effect of increasing free ammonia concentration (via experimental pH manipulation) on 24-hour rotifer survival in 5% ADE medium ($R^2$=0.48, $F_{1,18}$=16.3, p=0.0008). Solid line shows fit according to the prediction formula: ln(% survival)=3.606-0.0357*exposure time. (B) Effect of pH manipulation on 24-hour rotifer survival in ASW medium when a source of free ammonia is not added (p=0.93).
Figure 1B:
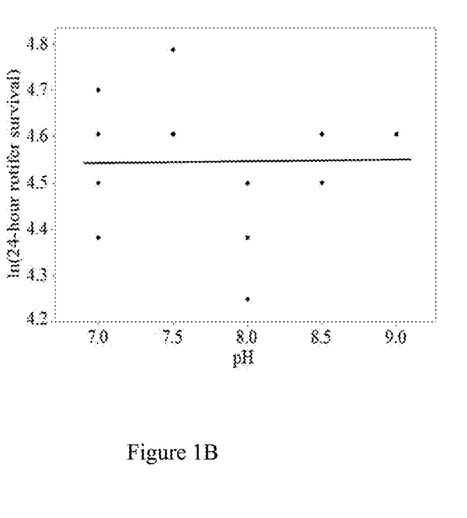

Elevated Free Ammonia Decreases *B. plicatilis* Survival in Defined Media and Dairy Wastewater There was a significant negative relationship between initial free ammonia concentration and *B. plicatilis* survival after 24 hours in both ASW medium ($R^2=0.59$, $F_{1,18}=26.1$, $p<0.0001$) and 5% dairy ADE (FIG. 1A, $R^2=0.48$, $F_{1,18}=16.3$, $p=0.0008$). Additionally, there was no effect of pH on the survival of *B. plicatilis* in the control ASW cultures to which ammonium was not added (FIG. 1B, $R^2=0.0005$, $F_{1,18}=0.0082$, $p=0.93$). This indicates that increased free ammonia concentration is the primary driver of rotifer mortality and that pH effects on *B. plicatilis* survival are minimal. These data also confirm that the concentrations of ammonium and pH levels used yield a free ammonia concentration which is adequate to significantly reduce rotifer populations after just 24 hours.

These observations support the results of other studies which have found a significant effect of free ammonia concentrations on *Brachionus* rotifer survival (Lincoln et al., 1983; Schlüter and Groeneweg, 1985). This body of support for the concept of controlling rotifers with free ammonia justifies the approach we employ regarding the manipulation of exposure time with the goal of optimizing algal growth while simultaneously limiting rotifer contamination.

Free Ammonia Levels that Inhibit *B. plicatilis* do not Inhibit *N. oculata*

Figure 2:
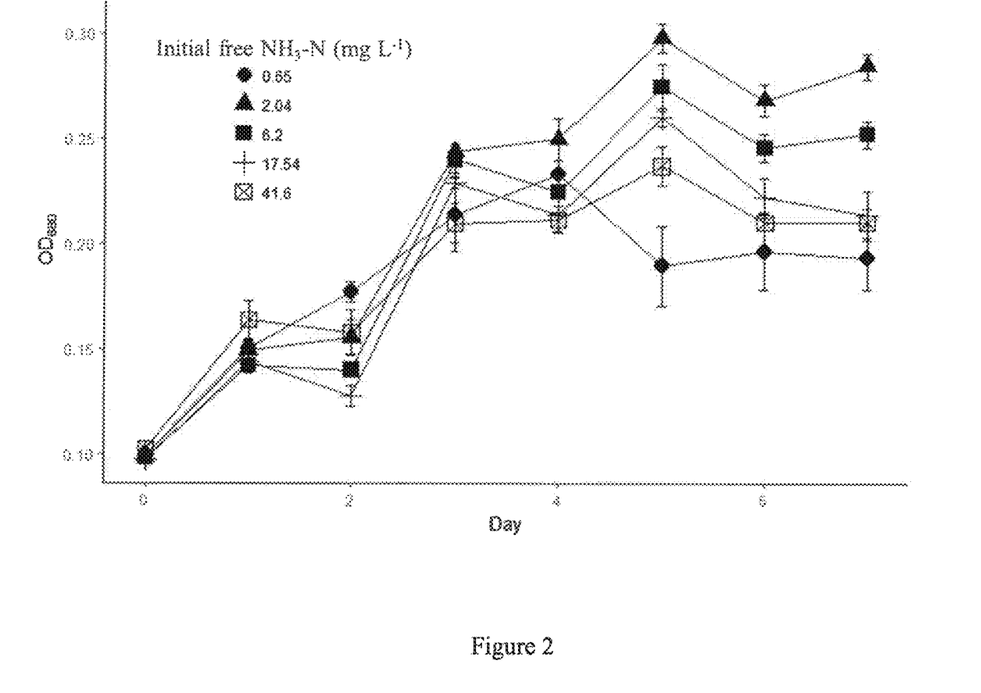
FIG. 2 is a graph showing *N. oculata* density over time, as measured by $OD_{680}$, when grown in 5% ADE medium. Five different initial pH levels were used, resulting in a gradient of five different free ammonia levels which increased as pH increased. Specifically, free ammonia concentrations were 0.65 mg $L^{-1}$ (at pH 7), 2.04 mg $L^{-1}$ (at pH 7.5), 6.2 mg $L^{-1}$ (at pH 8), 17.54 mg $L^{-1}$ (at pH 8.5), and 41.6 mg $L^{-1}$ (at pH 9).

There was no observed inhibition of *N. oculata* in either f/2 or ADE media at any of the free ammonia levels tested (FIG. 2). Neither endpoint $OD_{680}$ levels nor specific growth rates were significantly altered in response to increasing free ammonia levels. In fact, $OD_{680}$ levels of *N. oculata* increased with increasing free ammonia levels (note: this means higher pH levels as well) when grown in f/2 medium ($R^2=0.57$, $F_{1,18}=24.1$, $p=0.0001$). For the ADE cultures, free ammonia concentration had no effect on final $OD_{680}$ levels (FIG. 2, $R^2=0.11$, $F_{1,18}=2.26$, $p=0.15$). Similarly, there was no effect of initial free ammonia on growth rates in either f/2 medium ($R^2=0.03$, $F_{1,18}=0.51$, $p=0.48$) or ADE medium ($R^2=0.0005$, $F_{1,18}=0.009$, $p=0.93$). This suggests that, unlike for B. plicatilis, free ammonia levels in this experiment are not the primary driver of growth for N. oculata, and that alteration of pH is likely to have a stronger influence on algal growth.

These data confirm the results of previous research indicating that higher tolerance for free ammonia in algae than in certain grazers can be a potentially useful tool for algal crop protection. While ammonia inhibition of algae has been noted at relatively low levels for certain algal species (Abeliovich and Azov, 1976; Gutierrez et al., 2016), we report no evidence to suggest that N. oculata was inhibited at the free ammonia levels which significantly reduced B. plicatilis survival in this study. Instead, it appears that pH may have been more influential in the growth of N. oculata, which achieves optimal growth at a pH of 8 to 9 (Bartley et al., 2013), possibly explaining our observed increase in growth with higher pH/higher free ammonia. This indicates, however, that both the pH and free ammonia levels used in this study could treat rotifer contamination while maintaining optimal growth conditions for N. oculata.

Optimization of Free Ammonia Exposure Time

Figure 3:
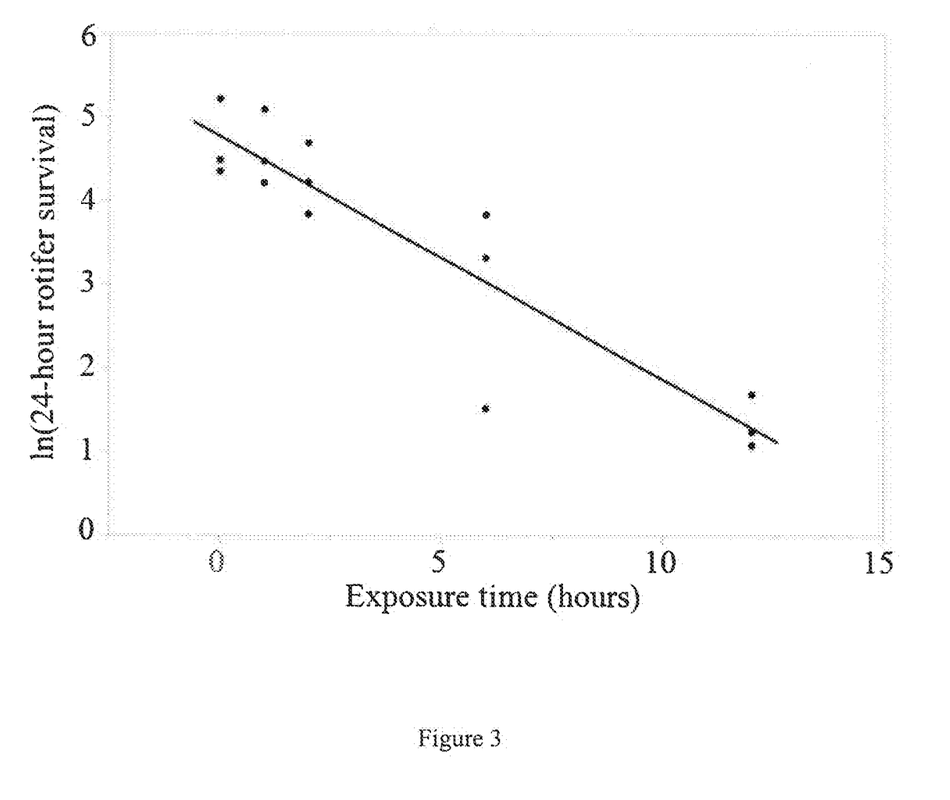
FIG. 3 is a graph showing effect of exposure time to elevated (52.8 mg $L^{-1}$) free ammonia on 24-hour *B. plicatilis* survival in ADE medium ($R^2$=0.84, $F_{1,13}$=70.7, p<0.0001). Points show individual experimental replicates. Solid line shows fit according to the prediction formula: ln(% survival)=4.768-0.2902*exposure time.
Figure 4:
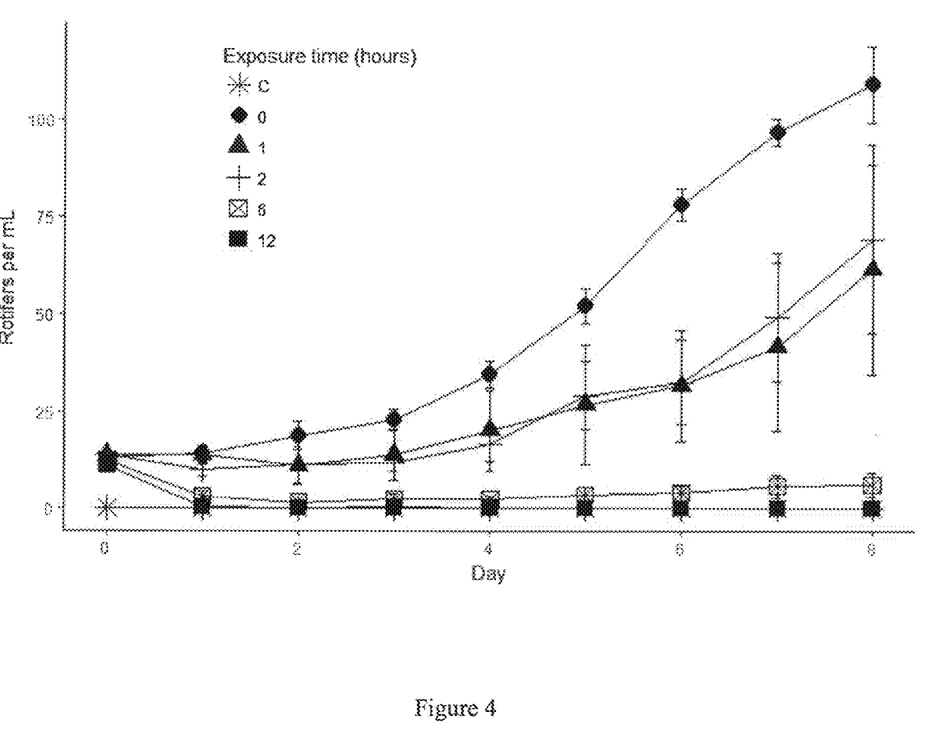
FIG. 4 is a graph showing densities of *B. plicatilis* during the eight day experiment for each exposure time to elevated free ammonia in ADE medium. C: rotifer-free control. Points and bars represent mean±SEM and symbols represent different exposure times in hours.
Figure 5:
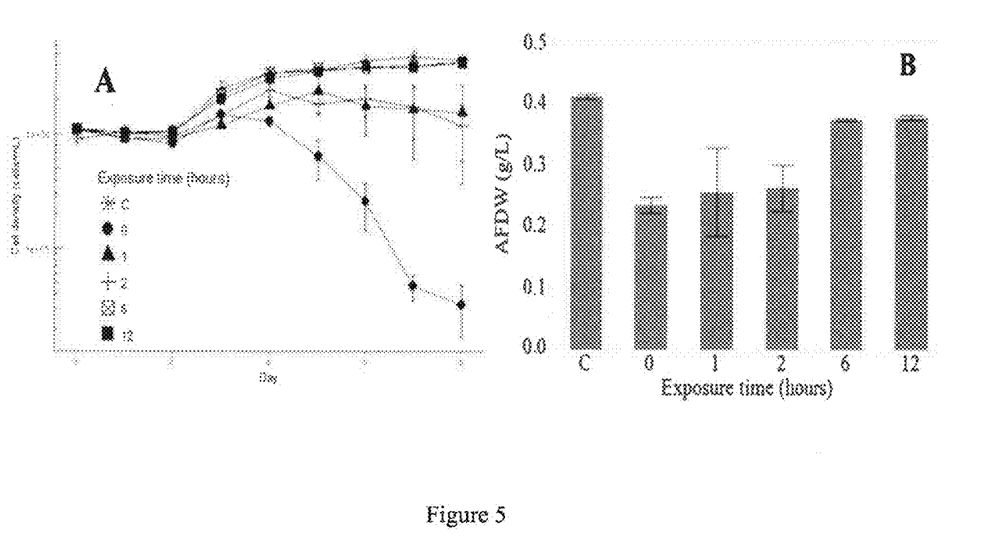

The different exposure times used in this experiment resulted in marked differences in rotifer survival and reproduction. Elevated free ammonia exposure time significantly decreased 24-hour rotifer survival in both f/2 medium ($R^2=0.48$, $F_{1,13}=12.0$, $p=0.0042$) and dairy ADE medium (FIG. 3, $R^2=0.84$, $F_{1,13}=70.7$, $p<0.0001$). Moreover, these reductions in B. plicatilis densities were maintained over the course of both eight-day experiments; in both f/2 and ADE media, mean rotifer densities for six- and twelve-hour exposure times remained below the initial density (FIG. 4). Conversely, rotifer cultures receiving two hours or less of exposure in ADE medium proliferated, with up to an order of magnitude increase in rotifer density (FIG. 4). This led to significant differences in final algal biomass in terms of both cell density (FIG. 5, Welch's ANOVA, $F_{5,4.72}=257.1$, $p<0.0001$) and AFDW (FIG. 5B), Welch's ANOVA, $F_{5,5.27}=27.7$, $p=0.0009$)). Algal cell densities for the cultures with no free ammonia exposure experienced a decline of two orders of magnitude and were 99% lower in cell density than those which experienced a six-hour free ammonia exposure time. Essentially, in the absence of a significant free ammonia exposure and in the presence of rotifers, the algal cultures crashed due to the top-down grazing pressure of the rotifers. However, with sufficient ammonia exposure, these crashes were prevented, allowing algae to remain at high density.

These results indicate that for the levels of free ammonia we employed, a six-hour exposure time is an optimal threshold for reducing rotifer contamination while maintaining high levels of algal biomass productivity. Indeed, we did not detect any differences between the final AFDW of the rotifer-free control ($0.41\pm0.007$ g $L^{-1}$) and either the 6-hour ($0.37\pm0.004$ g $L^{-1}$) or 12-hour ($0.38\pm0.004$ g $L^{-1}$) exposure time treatments. Similarly, no differences in algal growth rates were detected between the rotifer-free control ($0.67\pm0.06$ $d^{-1}$) and either the 6-hour ($0.70\pm0.01$ $d^{-1}$) or 12-hour ($0.60\pm0.06$ $d^{-1}$) exposure time treatments, which suggests that for these treatments ammonia toxicity did not affect N. oculata but did cause acute toxicity in B. plicatilis rotifers.

While these results are promising, grazer responses to free ammonia concentrations are species-specific (Gutierrez et al., 2016). It is reasonable to conclude effectiveness with other organisms and additional research would verify free ammonia concentrations and/or exposure times that will optimally reduce the grazer of interest while leaving the algal cultivar uninhibited. Effects of the frequency of ammonia exposure can have significant effects on toxicity in fish (Milne et al., 2000); however this has not been tested for algae-grazer systems and could therefore further enhance optimization of ammonia-based grazer control.

Further experimentation will show effects of algal physiological state, growth stage, and cell density on inhibition of algae by free ammonia, as more dilute cultures could potentially be affected at different concentrations than more dense cultures. Finally, this approach of ammonia-based control could be coupled with fluorescence-based techniques (Markou et al., 2016) to adaptively manage mass algal cultures to prevent ammonia toxicity in more susceptible algal species while still inhibiting the growth of harmful aquatic pests.

Remarks

We show that N. oculata is unaffected by free ammonia levels which significantly reduce B. plicatilis rotifer survival and provide an optimization of ammonia-based crop protection via manipulation of exposure time to elevated ammonia (41.6 to 52.8 mg $L^{-1}$ free $NH_3$—N). Of the levels tested (0, 1, 2, 6, and 12 hours of exposure), the 6-hour and 12-hour treatments most effectively suppressed rotifer pests and exhibited no negative effects on algal growth. This crop protection strategy may be used to increase annual yields in ammonia-rich open pond cultivation systems where pond collapse induced by grazing pests threatens productivity and stability.

Acknowledgements

We would like to thank Dr. M. Lytle for analysis of ammonia samples. This research was funded by USDA-NIFA Award #2012-68002-19952.

REFERENCES

Abeliovich, A., Azov, Y., 1976. Toxicity of ammonia to algae in sewage oxidation ponds. Appl. Envir. Microbiol. 31, 801-806.

Arthur, J. W., West, C. W., Allen, K. N., Hedtke, S. F., 1987. Seasonal toxicity of ammonia to five fish and nine invertebrate species. Bull. Environ. Contam. Toxicol. 38, 324-331. doi:10.1007/BF01606682

Bartley, M. L., Boeing, W. J., Corcoran, A. A., Holguin, F. O., Schaub, T., 2013. pH effects on growth and lipid accumulation of the biofuel microalgae Nannochloropsis salina and invading organisms. Biomass and Bioenergy 54, 83-88. doi:10.1016/j.biombioe.2013.03.026

Carney, L. T., Lane, T. W., 2014. Parasites in algae mass culture. Front. Microbiol. 5, 278. doi:10.3389/fmicb.2014.00278

Chisti, Y., 2008. Biodiesel from microalgae beats bioethanol. Trends Biotechnol. 26, 126-31. doi:10.1016/j.tibtech.2007.12.002

Chisti, Y., 2007. Biodiesel from microalgae. Biotechnol. Adv. 25, 294-306. doi:10.1016/j.biotechadv.2007.02.001

Day, J. G., 2013. Grazers: the overlooked threat to the sustained production of future algal biofuels. Biofuels 4, 459-461. doi:10.4155/bfs.13.29 de Araujo, A., Snell, T. W., Hagiwara, A., 2000. Effect of unionized ammonia, viscozity and protozoan contamination on the enzyme activity of the rotifer *Brachionus plicalitis*. Aquac. Res. 31, 359-365.

Gersich, F. M., Hopkins, D. L., 1986. Site-Specific Acute and Chronic Toxicity of Ammonia To *Daphnia Magna* Straus. Environ. Toxicol. Chem. 5, 443. doi:10.1897/1552-8618 (1986) 5[443:SAACTO]2.0.CO;2

Gutierrez, J., Kwan, T. A., Zimmerman, J. B., Peccia, J., 2016. Ammonia inhibition in oleaginous microalgae. Algal Res. 19, 123-127. doi:10.1016/j.algal.2016.07.016

Jones, C. S., Mayfield, S. P., 2012. Algae biofuels: versatility for the future of bioenergy. Curr. Opin. Biotechnol. 23, 346-51. doi:10.1016/j.copbio.2011.10.013

Lincoln, E. P., Hall, T. W., Koopman, B., 1983. Zooplankton control in mass algal cultures. Aquaculture 32, 331-337. doi:10.1016/0044-8486(83)90230-2

Markou, G., Depraetere, O., Muylaert, K., 2016. Effect of ammonia on the photosynthetic activity of Arthrospira and *Chlorella*: A study on chlorophyll fluorescence and electron transport. Algal Res. 16, 449-457. doi:10.1016/j.algal.2016.03.039

Milne, I., Seager, J., Mallett, M., 2000. Effects of short-term pulsed ammonia exposure on fish. Environ. Toxicol. Chem. 19, 2929-2936. doi:10.1897/1551-5028 (2000) 019<2929:EOSTPA>2.0.CO;2

Montagnes, D. J. S., Kimmance, S. A., Tsounis, G., Gumbs, J. C., 2001. Combined effect of temperature and food concentration on the grazing rate of the rotifer *Brachionus plicatilis*. Mar. Biol. 139, 975-979. doi:10.1007/s002270100632

Passero, M., Cragin, B., Coats, E. R., McDonald, A. G., Feris, K., 2015. Dairy Wastewaters for Algae Cultivation, Polyhydroxyalkanote Reactor Effluent Versus Anaerobic Digester Effluent. BioEnergy Res. 8, 1647-1660. doi: 10.1007/s12155-015-9619-9

Pimentel, D., 2005. Environmental and Economic Costs of the Application of Pesticides Primarily in the United States. Environ. Dev. Sustain. 7, 229-252.

Pradeep, V., Van Ginkel, S., Park, S., Igou, T., Yi, C., Fu, H., Johnston, R., Snell, T., Chen, Y., 2015. Use of Copper to Selectively Inhibit *Brachionus calyciflorus* (Predator) Growth in *Chlorella kessleri* (Prey) Mass Cultures for Algae Biodiesel Production. Int. J. Mol. Sci. 16, 20674-20684. doi:10.3390/ijms160920674

Schlüter, M., Groeneweg, J., 1985. The inhibition by ammonia of population growth of the rotifer, *Brachionus rubens*, in continuous culture. Aquaculture 46, 215-220.

Shurin, J. B., Abbott, R. L., Deal, M. S., Kwan, G. T., Litchman, E., McBride, R. C., Mandal, S., Smith, V. H., 2013. Industrial-strength ecology: trade-offs and opportunities in algal biofuel production. Ecol. Lett. 16, 1393-1404. doi:10.1111/ele.12176

Tan, X.-B., Zhang, Y.-L., Yang, L.-B., Chu, H.-Q., Guo, J., 2015. Outdoor cultures of *Chlorella pyrenoidosa* in the effluent of anaerobically digested activated sludge: The effects of pH and free ammonia. Bioresour. Technol. 200, 606-615. doi:10.1016/j.biortech.2015.10.095

Van Ginkel, S. W., Igou, T., Hu, Z., Narode, A., Cheruvu, S., Doi, S., Johnston, R., Snell, T., Chen, Y., 2015. Taking advantage of rotifer sensitivity to rotenone to prevent pond crashes for algal-biofuel production. Algal Res. 10, 100-103. doi:10.1016/j.algal.2015.03.013

Walsh, B. J., Rydzak, F., Palazzo, A., Kraxner, F., Herrero, M., Schenk, P. M., Ciais, P., Janssens, I. A., Peñuelas, J., Niederl-Schmidinger, A., Obersteiner, M., 2015. New feed sources key to ambitious climate targets. Carbon Balance Manag. 10, 26. doi:10.1186/s13021-015-0040-7

Wang, L., Li, Y., Chen, P., Min, M., Chen, Y., Zhu, J., Ruan, R. R., 2010. Anaerobic digested dairy manure as a nutrient supplement for cultivation of oil-rich green microalgae *Chlorella* sp. Bioresour. Technol. 101, 2623-8. doi: 10.1016/j.biortech.2009.10.062

Xu, C., Wu, K., Van Ginkel, S., Igou, T., Lee, H., Bhargava, A., Johnston, R., Snell, T., Chen, Y., 2015. The Use of the Schizonticidal Agent Quinine Sulfate to Prevent Pond Crashes for Algal-Biofuel Production. Int. J. Mol. Sci. 16, 27450-27456. doi:10.3390/ijms161126035

What is claimed is:

1. A method of inhibiting live rotifer comprising *Brachionus plicatilis* or *Philodina* in an algae composition comprising *Nannochloropsis oculata* without inhibiting said algae in said composition, the method comprising:
   i) contacting said composition with dairy production wastewater comprising free ammonia; and then
   ii) maintaining pH of the composition obtained from the step i) at a level of at least 8 for six to 12 hours so as to maintain the free ammonia at a level capable of reducing a number of said live *Brachionus plicatilis* or *Philodina* rotifer in the obtained composition, thereby inhibiting said rotifer.

2. The method of claim 1, wherein said pH is 8 to 9.

3. The method of claim 1, wherein said pH is 9.

4. The method of claim 1, wherein the number of said live *Brachionus plicatilis* or *Philodina* rotifer is reduced to zero.

5. The method of claim 1, wherein said live rotifer is inhibited and said algae are not inhibited without addition of additional ammonia or chemicals.

6. A method of inhibiting rotifer comprising live *Brachionus plicatilis* or *Philodina* in an algae composition comprising *Nannochloropsis oculata* and increasing concentration of algae in said composition, the method comprising:
   i) contacting said composition with dairy production wastewater comprising free ammonia; and then
   ii) maintaining pH of the composition obtained from the step i) at a level of at least 8 for six to 12 hours so as to maintain the free ammonia at a level capable of reducing a number of said live *Brachionus plicatilis* or *Philodina* rotifer in the obtained composition, thereby inhibiting said rotifer and increasing the concentration of said *Nannochloropsis oculata* algae.

7. The method of claim 6, wherein the number of said live rotifer is reduced to zero.

8. A method of reducing algae production costs, the method comprising:
   i) providing an algae composition comprising *Nannochloropsis oculata*, wherein live rotifer comprising *Brachionus plicatilis* or *Philodina* is present in said algae composition;
   ii) contacting said algae composition with dairy production wastewater comprising free ammonia;
   iii) maintaining pH of the composition obtained from the step ii) at a level of at least 8 for more than two hours so as to maintain the free ammonia at a level capable of reducing a number of said live *Brachionus plicatilis* or *Philodina* rotifer in the obtained composition, thereby inhibiting said rotifer without inhibition of said algae, without the need to add additional ammonia or chemicals; and then
   iv) harvesting said algae.

* * * * *